United States Patent [19]

von Oppolzer

[11] Patent Number: 5,132,428

[45] Date of Patent: Jul. 21, 1992

[54] PROCESS FOR PREPARING ENANTIOMERICALLY PURE ALPHA-AMINO ACIDS

[75] Inventor: Wolfgang W. R. E. J. von Oppolzer, Vandoeuvres, Switzerland

[73] Assignee: BP Chemicals Limited, London, England

[21] Appl. No.: 609,432

[22] Filed: Nov. 5, 1990

[30] Foreign Application Priority Data

Nov. 9, 1989 [GB] United Kingdom ............... 8925368

[51] Int. Cl.$^5$ .................. C07D 275/04; C07C 29/08; C07B 53/00
[52] U.S. Cl. .................................... 548/207; 548/208; 562/401; 562/575
[58] Field of Search ............... 548/207, 208; 562/401, 562/575

[56] References Cited

PUBLICATIONS

Oppolzer et al., Tetrahedron Letters, vol. 30, No. 44, pp. 6009–6010, 1989.
March, Advanced Organic Chemistry 3rd Ed, pp. 411–412, 1985.
Oppolzer, Tetrahedron, vol. 43, No. 18, pp. 1970–2002, 1987.
Chemical Abstracts, vol. 113, No. 3, Jul. 16, 1990, Columbus, Ohio, USA Oppolzer, W. et al. "Asymmetric alkylation of a sultam-derived glycinate equivalent: practical preparation of enantiomerically pure alpha-amino acids" p. 719, col. 1, abstract no. 24 463f. & Tetrahedron Lett. 1989, 30 (44), 6009–10.
Chemical Abstracts, vol. 108, No. 9, Feb. 29, 1988, Columbus, Ohio, USA—Seebach D. et al "Addition of chiral glycine, methionine, and vinylglycine enolate derivatives to aldehydes and Ketones in the preparation of enantiomerically pure alpha-amino-betahydroxy acids" p. 725, col. 1, abstract no. 75 788v and Helv.-Chim.Acta 1987, 70(1) 239–61.

*Primary Examiner*—Joseph Paul Brust
*Assistant Examiner*—M. S. H. Gabilan
*Attorney, Agent, or Firm*—Brooks Haidt Haffner & Delahunty

[57] ABSTRACT

A process for enantioselectively alkylating, at the asterisked carbon atom, a single enantiomer of a glycine derivative having the general formula ZCOCH(R)NY wherein Z is a moiety derived from a chiral sultam, R is hydrogen or $C_1$ to $C_{10}$ alkyl and Y is one or more groups rendering the nitrogen atom unreactive towards alkylating agents comprises:

(i) reacting the glycine derivative with an enolising agent to produce the corresponding enolate of the glycine derivative, and (ii) thereafter reacting the enolate of the glycine derivative with an alkylating agent of formula $R^1X$ to generate a single enantiomer of a product of formula $ZCOC(R)(R^1)NY$ where $R^1$ is selected from $C_1$ to $C_{10}$ alkyl, $C_1$ to $C_{20}$ aralkyl, $C_2$ to $C_{10}$ alkenyl or substituted derivatives thereof and X is Cl, Br or I. The product of the process can be treated with first acid and then base to generate the enantiomerically pure alpha-amino acid of formula $HO_2CC(R)(R^1)NH_2$ and a single enantiomer of the chiral sultam ZH. Preferred examples of the chiral sultam moiety Z are

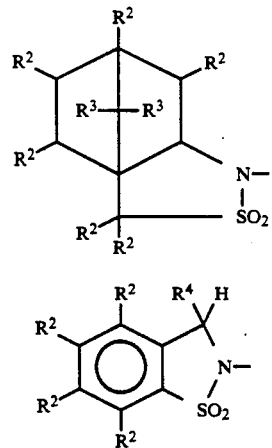

where $R^2$ and $R^3$ are independently hydrogen or $C_1$ to $C_{10}$ alkyl and $R^4$ is $C_1$ to $C_{20}$ alkyl.

7 Claims, No Drawings

PROCESS FOR PREPARING ENANTIOMERICALLY PURE ALPHA-AMINO ACIDS

The present invention relates to the preparation of enantiomerically pure alpha-amino acids from glycine or a substituted derivative thereof.

It has been found that glycine or a substituted derivative thereof can be converted into a range of enantiomerically pure alpha-amino acids by a process which involves, as a key step, the stereospecific alkylation of a glycine moiety. Stereospecificity is achieved by attaching the glycine moiety to a single anantiomer of a chiral sultam prior to alkylation. The chiral sultam then acts as a chiral auxiliary directing the alkylation of the glycine moiety.

According to the present invention there is provided a process for enantioselectively alkylating, at the asterisked carbon atom, a single enantiomer of a glycine derivative having the general formula ZCOCH(R)NY wherein Z is a moiety derived from a chiral sultam, R is hydrogen or $C_1$ to $C_{10}$ alkyl and Y is one or more groups rendering the nitrogen atom unreactive towards alkylating agents which process comprises:

(i) reacting the glycine derivative with an enolising agent to produce the corresponding enolate of the glycine derivative, and (ii) thereafter reacting the enolate of the glycine derivative with an alkylating agent of formula $R^1X$ to generate a single enantiomer of a product of formula $ZCOC(R)(R^1)NY$ where $R^1$ is selected from $C_1$ to $C_{10}$ alkyl, $C_1$ to $C_{20}$ aralkyl, $C_2$ to $C_{10}$ alkenyl or substituted derivatives thereof and X is Cl, Br or I.

It is a feature of the process of the present invention that the alkylation reaction is enantioselective at the asterisked carbon notwithstanding that the alkylating agent is not necessarily itself chiral. The process of the present allows optical purities of greater than 95% to be routinely achieved with a wide range of alkylating agents.

Although in principle any chiral sultam can supply the chiral moiety Z- one particularly convenient family of moieties are those having the general formula:

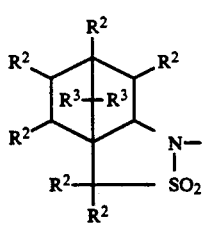

where the $R^2$ and $R^3$ groups are independently hydrogen or $C_1$ to $C_{10}$ alkyl. Most preferred are those moieties where the $R^2$ groups are hydrogen and the $R^3$ groups are methyl.

Another convenient family of moieties are those having the general formula:

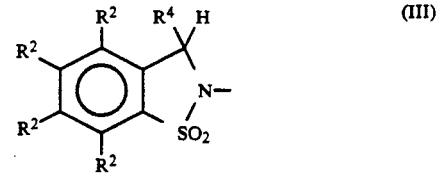

wherein the $R^4$ group is $C_1$ to $C_{20}$ alkyl or aryl substituted alkyl.

Most preferred examples of this class are those moieties in which $R^4$ is either (a) $C_1$ to $C_6$ unsubstituted primary alkyl groups in which the terminal carbon atom is substituted with phenyl or alkyl substituted phenyl or alkyl substituted phenyl or (b) $C_1$ to $C_6$ secondary or tertiary alkyl groups or $C_1$ to $C_6$ secondary or tertiary alkyl groups in which the secondary or tertiary carbon atom bonded to the rest of the moiety is substituted with one or more phenyl groups.

The single enantiomer of the glycine derivative of formula (I) can be prepared by reacting a single enantiomer of the corresponding chiral sultam ZH with a molecule of formula $QOCCH(R)NY$ wherein Q is selected from Cl br, I or $OR^2$. The reaction with $Q=OR^2$ is suitably carried out in a dry solvent in the presence of a Group III metal alkyl (eg $(CH_3)_3Al$).

The nitrogen atom in the glycine derivative is protected by the protecting moiety Y. A well known and very convenient way of protecting amines is to convert them to the corresponding Schiff base hence it is preferred than Y has the formula $=C(B^1)_2$ where the $B^1$ groups are independently hydrogen, aryl, alkyl or thioalkyl. Preferably the $B^1$ groups are both $C_1$ to $C_4$ thioalkyl.

The process of the present invention, as mentioned above, comprises two stages. In the first stage, the glycine derivative is reacted with an enolising agent. Typical enolising agents are metal alkyls. Examples of suitable metal alkyls are the $C_1$ to $C_6$ alkyl derivatives of Group IA, IIA and IIIA metals.

The first stage of the process is typically effected at a temperature below $0°$ C., preferably below $-25°$ C. in an ethereal solution. Another possibility is the use of a two phase system (eg aqueous base and a chlorinated solvent) in the presence of a phase transfer agent such as n-Bu$_4$NHSO$_4$.

The product of the first stage is preferably used in situ without isolation. In the second stage, this product is treated with the alkylating agent to generate the product.

Preferred alkylating agents $R^1X$ are the iodide or bromide derivatives. The reaction is again preferably carried out at a temperature below $0°$ C.

The product of the second stage, having the formula $ACOC(R)(R^1)NY$ can be converted into the corresponding single enantiomer of an alpha-amino acid by a two stage process which involves (a) converting the product of the second stage into the amine $ZCOC(R)(R^1)NH_2$ and (b) converting the amine into the alpha-amino acid $HO_2CC(R)(R^1)NH_2$. Step (a), in the case of Y being as described above, involves an acid catalysed hydrolysis reaction whilst step (b) in which the moiety Z is removed and the chiral sultam ZH regenerated can be effected by treatement with base to yield a metal salt of the alpha-amino acid followed by ion-exchange, eg with an appropriate acidic ion-exchange resin.

The process is now illustrated by the following Examples.

EXAMPLE 1

Preparation of N-(Bis(methylthio) methylene) glycine methyl ester

This compound was prepared from the methyl ester of glycine using standard techniques.

EXAMPLE 2

Preparation of (2R)-N-(N$^1$-Bis(methylthio methyleneglycl) bornane-2-10-sultam 5.38g (25mol) of 2R-bornane-2,10-sultam was stirred at 50° C. for 24 hours with 1.5 equivalents of the product of Example 1. Fractional Crystallisation (hexane/Et$_2$O 1:2), followed by crystallistion (twice from ethanol) yielded the desired product as slightly yellow crystals (8.13g, 21.6mmol 86%). Melting point 107°-109° C., Rotation (c=3.27) [alpha]$_D$ = -115.6°.

Alternatively the desired product can be prepared by adding 1.2 e.g. of a solution of trimethylaluminium in hexane (2M) dropurlse at room temperature to a solution of the sultam in toluene (2ml/mmol). After 15 minutes the product of Example 1 (1.2-1.6 eq) in toluene (0.5ml/mmol) is added. The reaction mixture is then heated to 60° C. until reaction is complete, cooled to room temperature and methanol (1ml/mmol) is added slowly. After stirring for 1 hour. The product is filtered through celite, worked up with ethyl acetate dried and crystallised.

General Procedure for Enantioselectively Alkylating the Product of Example 2 n-butyllithium (1.1 eq) was added dropwise over a period of 1 hour to a cold (-78° C.) solution of the product of Example 2 in THF (5ml/mmol). After stirring for 1 hour at -78° C., the alkylating agent (3 eq) in hexamethylphosphoramide (HMPA-3 eq) was added. The mixture was allowed to stir overnight, slowly warmed to room temperature and then quenched with water. The product was worked up with diethyl ether and fractional crystallisation.

EXAMPLE 3

(2R,2'S)-N-(N'-Bis(methylthio)methylene-B-phenylalanyl)borane-2,10-sultam

The product of Example 2 (377 mg, 1 mmol) was converted by using the general procedure and benzyl iodide as alkylating agent. The reaction was stirred at -55° C. overnight. FC (Hex/Et$_2$O 1:1) was followed by crystallisation. (EtOH) to afford the product as white crystals (435 mg, 0.93 mmol, 93%, yield after FC: 96%); crude d.e.=94.7% (99% after cryst.). M.p. 132°-133° C. Rotation (c=1.56): [alpha]$_D$= -109.2°, [alpha]$_{578}$=114.1°, [alpha]$_{546}$= -228.0°, [alpha]$_{365}$= -376.8°.

EXAMPLE 4

(2R,2'S)-N-(N'-Bis(methylthio)methylenealanyl)bornane-2,10-sultam

The product of Example 2 (377 mg, 1 mmol) was converted by using the general procedure and methyl iodide as alkylating agent. The reaction was stirred overnight at -50° C. Direct cryst. (hexanes) affords the product as white crystals (340 mg, 0.87 mmol, 87%); crude d.e.=96.4% (99% after cryst.), M.p.=119°-120° C. Rotation (c=21.34): [alpha]$_D$= -70.1°, [alphax]$_{576}$= -72.8°, [alpha]$_{546}$= -82.6°, [alphax]$_{436}$= -138.6°, [alphax]$_{365}$= -216.6°.

EXAMPLE 5

(2R,2'S)-N-(N'-Bis(methylthio)methylenealanyl)bornane-2,10-sultam

The product of Example 2 (377 mg, 1 mmol) was converted by using the general procedure and allyl iodide as alkylating agent. The reaction was stirred at -50° C. overnight. FC (hex/Et$_2$O 3.4) was followed by crystallisation. (MeOH) to afford the product as white crystals (364 mg, 0.87 mmol, 87%; yield after FC: 94%); crude d.e.=96.8%(99% after cryst.). GC (HP-1): 12.90 (minor), 13.47 (major).

EXAMPLE 6

(2R,2'S)-N-(N'-Bis(methylthio)methyleneamino-3'-tert-butoxycarbonyl propionyl)bornane-2,10-sultam The product of Example 2 (377 mg, 1 mmol) was converted by using the general procedure and t-butyl alpha-bromoacetate +(n-Bu)$_4$NI (0.1 eq.) as alkylating agent. FC (hex/Et$_2$O 1:1) was followed by crystallisation. (EtOH) to afford the product as white crystals (453 mg, 0.96 mmol, 96%; yield after FC: 100%); crude d.e.=98.4% (99% after cryst.). M.p. 142°-144° C. Rotation (c=21.19): [alpha]$_D$=36.1°, [alpha]$_{576}$= -37.6°, [alpha]$_{576}$= -42.4°, [alpha]$_{436}$=68.7°, [alpha]$_{365}$= -97.4°.

EXAMPLE 7

(2R,2'S)-N-(N'-Bis(methylthio)methylenenorleucyl)-bornane-2,10-sultam

The product of Example 2 (377 mg, 1 mmol) was converted by using the general procedure with n-butyl iodide as alkylating agent. 7 eq. of HMPA were used in this case. FC hex/Et$_2$O 1:1) was followed by crystallisation (hexanes) to afford the product as white crystals (372 mg, 0.86 mmol, 86%; yield after FC: 89%); crude d.e.=97.1% (99% after cryst.). M.p. 95°-97° C. Rotation (c=1.70); [alpha]$_D$= -71.5°, [alpha]$_{576}$= -74.3°, [alpha]$_{546}$= -84.5°, [alpha]$_{436}$=143.5°, [alpha]$_{365}$= -229.2°.

EXAMPLE 8

(2R,2'S)-N-(N'-Bis(methylthio)methyleneleucyl)bornane-2,10-sultam

The product of Example 2 (377 mg, 1 mmol) was converted by using the general procedure with i-butyl iodide (5 eq.) as alkylating agent. 7 eq. of HMPA were used. FC (hex/Et$_2$O 1:1) was followed by crystallisation. (EtOH) to give the product as white crystals (367 mg, 0.85 mmol, 85%; yield after FC: 87%); crude d.e.=95.6% (99% after cryst.). M.p. 125°-127° C. Rotation (c=1.08):[alpha]$_D$= -82.4°, [alpha]$_{578}$= -85.9°, [alpha]$_{546}$=97.8°, [alpha]$_{436}$= -167.6°, [alphax]$_{365}$=271.0°.

General Procedure for Converting the Products of Examples 3 to 8 to the Corresponding Alpha-amino Acid The starting material was dissolved in THF (10-20 ml/mmol). 1N aq. HCl (10 ml/mmol) was added and the solution was stirred at RT for 24 hours. The THF was evaporated. The reaction was washed with Et$_2$O and water evaporated. The white solid residue was dissolved in THF (20 ml/mmol) and water (10 ml/mmol). LiOH.H₂O (4 eq.) was added and the solution stirred at RT for 24 hours. THF was then evaporated. The reaction was washed with CH₂Cl₂ (10 times). The combined org. phases were dried (MgSO₄) and concentrated to give pure sultam. The aq. layer was acidified to pH=1-2 with 1N aq. HCl, then resin Amberlite IR 120 (H-+ form, 7 g/mmol) was added and the mixture stirred at RT for 20 hours. The resin was then filtered and washed with distilled water until a test with 5% AgNO₃ showed no chloride left in the washings. The resin was then suspended in 6N aq. NH₄OH (50 ml/mmol) and stirred for 4 hours. Filtration, washing the resin with 6N aq. NH₄OH, evaporation of water and drying of the solid residue (at 0.01 mm) for several hours afforded pure alpha-amino acid.

TABLE

| Example No. | Starting material | Alpha-amino acid produced | Yield % | e.e |
|---|---|---|---|---|
| 9 | Product of Ex 3 | L-betaphenylalanine | 100 | 100 |
| 10 | Product of Ex 4 | L-alanine | 100 | 100 |
| 11 | Product of Ex 5 | L-allylglycine | 100 | 100 |
| 12 | Product of Ex 6 | L-aspartic acid | 75 | 100 |
| 13 | Product of Ex 7 | L-norleucine | 100 | 100 |
| 14 | Product of Ex 8 | L-Leucine | 100 | 99.5 |

EXAMPLE 9

(2R,2'S)-N-(N¹-Bis(methylthio) methylene-beta-phenylalanyl) bornane-2,10-sultam

Lithium hydroxide. H₂O (50eq) was added to a cold (−10° C.) mixture of Bu₄NHSO₄(1.2 eq) the product of Example 2 (1.1g, 2.9 mmol), benzyl iodide or benzyl bromide (1.2 eq) in CH₂cl₂ or toluene (10ml/mmol) and water (0.33 ml/mol). The resulting mixture was immediately sonicated for either 3 minutes (benzyl) iodide) or 4 minutes (benzyl bromide).

Sonication was carried out using a High Intensity Ultrasonic Processor (600-watt Model Sonics and Materials Inc) having a maximum processing capacity of 1000 ml solution, a standard horn and, 0.5 inch tip. The ultrasound tip was inserted into the middle of the reaction solution and continuous sonication applied with power monitor 18-20, output control 10 (actual power output ca b 75 watts).

After sonication the two phase mixture was filtered, evaporated and the residue dissolved in diethyl ether (50ml/mmol). the resulting solution was filtered to remove Bu₄NX, washed with water and brine, dried over anhydrous sodium sulphate and then evaporated. The resulting residue was then directly crystallised from ethanol and thereafter subjected to FC on silica gel (hex/Et₂O 2:1) to give white crystals of the desired product (from benzyl iodide 1.0482g, 2.33 mmol, 77.4%; crude d.e=90.7% (99.8% after cryst)), (from benzyl bromide 0.8603g, 1.85 mmol, 63.6% . crude d.e.=89% (99.8% after crystl)). M.P.=132°-133° C., Rotation (c=1.585): [alpha]$_d$= −109.2°, [alpha]$_{578}$= −114.0°, [alpha]$_{546}$= −130.2°, [alpha]$_{436}$= −227.4°, [alpha]$_{365}$= −109.2°.

The method of Example 9 can be applied to advantage when an activated halide is used as the alkylating method. The product of example 9 can be converted to the corresponding alpha amino acid using the method described above.

EXAMPLE 10

The methods of Examples 1, 2 and 9 were used to prepare the corresponding derivative employing the sultam moiety of formula (III) in which $R^4$ is methyl. In this example a single enantiomer of the sultam corresponding to the sultam moiety was used in place of 2R-bornane-2,10-sultam.

I claim:

1. A process for anantoiselectively alkylating, at the asterisked carbon atom, a single enantiomer of a glycine derivative having the general formula ZCOCH(R)NY wherein Z is a moiety derived from a chiral sultam, R is hydrogen or $C_1$ to $C_{10}$ alkyl and Y is one or more groups rendering the nitrogen atom unreactive towards alkylating agents which process comprises:
    (i) reacting the glycine derivative with an enolising agent to produce the corresponding enolate of the glycine derivative, and
    (ii) thereafter reacting the enolate of the glycine derivative with an alkylating agent of formula $R^1X$ to generate a single enantiomer of a product of formula ZCOC(R)(R¹)NY where $R^1$ is selected from $C_1$ to $C_{10}$ alkyl, $C_1$ to $C_{20}$ aralkyl, $C_2$ to $C_{10}$ alkenyl or substituted derivatives thereof and X is Cl, Br or I.

2. A process as claimed in claim 1 wherein the moiety Z has the general formula

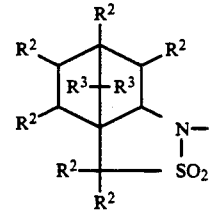

where $R^2$ and $R^3$ are independently hydrogen or $C_1$ $C_{10}$ alkyl.

3. A process as claimed in claim 2 wherein the $R^2$ groups are hydrogen and the $R^3$ groups are methyl.

4. A process as claimed in claim 1 wherein the moiety Z has the general formula

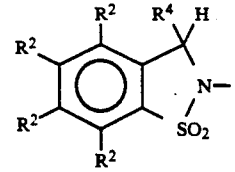

wherein the $R^2$ groups are independently hydrogen or $C_1$ to $C_{10}$ alkyl and $R^4$ is $C_1$ to $C_{20}$ alkyl.

5. A process as claimed in claim 4 where the $R^4$ group is either (a) $C_1$, to $C_6$ unsubstituted primary alkyl groups in which the terminal carbon atom is substituted with phenyl or alkyl substituted phenyl or (b) $C_1$ to $C_6$ secondary or tertiary alkyl groups or $C_1$ to $C_6$ secondary or tertiary alkyl groups in which the secondary or tertiary carbon atom bonded to the rest of the moiety is substituted with one or more phenyl groups.

6. A process as claimed in claim 1 comprising the additional step of (iii) hydrolysing the product of step (ii) with an acid catalyst.

7. A process as claimed in claim 6 comprising the additional step of (iv) removing the moiety Z from the product of step (iii) by treatment with base.

* * * * *

UNITED STATES PATENT AND TRADEMARK OFFICE
CERTIFICATE OF CORRECTION

PATENT NO. : 5,132,428

DATED : July 21, 1992

INVENTOR(S) : WOLFGANG W.R.E.J. von OPPOLZER

It is certified that error appears in the above-identified patent and that said Letters Patent is hereby corrected as shown below:

Col. 2, l. 25, correct the symbol --Br--

Col. 2, l. 56, correct the formula "ZCOC(R) $R^1$)NY"

Col. 3, last line, should read "(c=21.34):

Col. 5, l. 30, should read "(2R,2S)-N-"

Col. 5, l. 36, correct the formula "$CH_2\underline{Cl}_2$"

Col. 6, line 38, claim 2, change "$C_1$ $C_{10}$" to --$C_1$ to $C_{10}$--

Signed and Sealed this

Thirty-first Day of August, 1993

Attest:

BRUCE LEHMAN

Attesting Officer

Commissioner of Patents and Trademarks